(12) United States Patent
Li et al.

(10) Patent No.: US 11,152,096 B2
(45) Date of Patent: Oct. 19, 2021

(54) DETECTION SYSTEM AND DETECTION METHOD FOR INTRAVENOUS INJECTION LEAKAGE

(71) Applicant: BOE TECHNOLOGY GROUP CO., LTD., Beijing (CN)

(72) Inventors: Zhenglong Li, Beijing (CN); Lijie Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 1091 days.

(21) Appl. No.: 15/113,708

(22) PCT Filed: Jan. 8, 2016

(86) PCT No.: PCT/CN2016/070475
§ 371 (c)(1),
(2) Date: Jul. 22, 2016

(87) PCT Pub. No.: WO2017/008479
PCT Pub. Date: Jan. 19, 2017

(65) Prior Publication Data
US 2017/0157339 A1 Jun. 8, 2017

(30) Foreign Application Priority Data
Jul. 13, 2015 (CN) .......................... 201510409340.4

(51) Int. Cl.
*G16H 20/17* (2018.01)
*A61M 5/14* (2006.01)
(Continued)

(52) U.S. Cl.
CPC .............. *G16H 20/17* (2018.01); *A61M 5/14* (2013.01); *A61M 5/5086* (2013.01);
(Continued)

(58) Field of Classification Search
CPC .................................................. A61M 2205/15
See application file for complete search history.

(56) References Cited

U.S. PATENT DOCUMENTS 4,647,281 A * 3/1987 Carr .......................... A61B 5/01
343/718
4,877,034 A 10/1989 Atkins et al.
(Continued)

FOREIGN PATENT DOCUMENTS

CN 1541721 A 11/2004
CN 102078202 A 6/2011
(Continued)

OTHER PUBLICATIONS

Hadaway et al., "Infiltration and Extravasation: Preventing a complication of IV catheterization". AJN 2007, vol. 107, No. 8, pp. 64-72. (Year: 2007).*
(Continued)

*Primary Examiner* — Yi-Shan Yang
(74) *Attorney, Agent, or Firm* — Kinney & Lange, P.A.

(57) ABSTRACT

The present disclosure provides a detection system and a detection method for intravenous injection leakage. The detection system for intravenous injection leakage, includes a detection module, configured to detect a status parameter of a skin at an acupuncture point; and an analysis module, configured to acquire the status parameter, and to determine whether the intravenous injection leakage happens or not depending on the status parameter.

4 Claims, 3 Drawing Sheets

(51) Int. Cl.
*G16H 40/63* (2018.01)
*A61M 5/50* (2006.01)
*G06F 17/16* (2006.01)
*G16H 50/20* (2018.01)

(52) U.S. Cl.
CPC ............ *G06F 17/16* (2013.01); *G16H 40/63* (2018.01); *A61M 2205/13* (2013.01); *A61M 2205/15* (2013.01); *A61M 2205/18* (2013.01); *A61M 2205/3306* (2013.01); *A61M 2205/3317* (2013.01); *A61M 2205/3368* (2013.01); *A61M 2205/3553* (2013.01); *A61M 2205/3569* (2013.01); *A61M 2205/50* (2013.01); *A61M 2205/587* (2013.01); *G16H 50/20* (2018.01)

(56) References Cited

U.S. PATENT DOCUMENTS

| | | | |
|---|---|---|---|
| 5,947,910 A * | 9/1999 | Zimmet | A61M 5/16836 600/547 |
| 6,375,624 B1 * | 4/2002 | Uber, III | A61M 5/16836 128/DIG. 13 |
| 6,408,204 B1 | 6/2002 | Hirschman | |
| 6,751,500 B2 * | 6/2004 | Hirschman | A61B 5/0537 600/547 |
| 8,838,210 B2 | 9/2014 | Wood et al. | |
| 2003/0216663 A1 * | 11/2003 | Jersey-Willuhn | A61B 5/0536 600/547 |
| 2004/0171923 A1 * | 9/2004 | Kalafut | A61B 5/0059 600/407 |
| 2006/0173360 A1 * | 8/2006 | Kalafut | A61B 5/0059 600/478 |
| 2011/0125028 A1 | 5/2011 | Wood et al. | |
| 2012/0035856 A1 * | 2/2012 | Paradis | A61B 5/0059 702/19 |
| 2013/0131506 A1 * | 5/2013 | Pollack | A61M 5/158 600/431 |
| 2014/0213883 A1 * | 7/2014 | Banet | A61B 5/6802 600/395 |
| 2014/0303506 A1 | 10/2014 | Goldman et al. | |
| 2016/0089038 A1 * | 3/2016 | Chadderdon, III | A61B 5/02055 600/301 |
| 2019/0001129 A1 * | 1/2019 | Rosenbluth | A61N 1/0456 |

FOREIGN PATENT DOCUMENTS

| | | |
|---|---|---|
| CN | 202515664 U | 11/2012 |
| CN | 203042217 U | 7/2013 |
| CN | 104922755 A | 9/2015 |
| WO | 2009042562 A1 | 4/2009 |
| WO | WO-2009042562 A1 * | 4/2009 ........ A61M 5/16836 |

OTHER PUBLICATIONS

Extended European Search Report, for European Patent Application No. 16734166.8, dated Oct. 23, 2017, 8 pages.
Second Chinese Office Action, for Chinese Patent Application No. 2015104093404, dated Jan. 6, 2017, 9 pages.
International Search Report and Written Opinion (including English translation of Box V) dated Mar. 24, 2016, for corresponding PCT Application No. PCT/CN2016/070475.
First Chinese Office Action dated Jun. 20, 2016, for corresponding Chinese Application No. 201510409340.4.

* cited by examiner

DETECTION SYSTEM AND DETECTION METHOD FOR INTRAVENOUS INJECTION LEAKAGE

BACKGROUND OF THE INVENTION

Field of the Invention

The present application relates to the technical field of medical apparatus and instruments, and particularly, to a detection system and a detection method for intravenous injection leakage.

Description of the Related Art

An intravenous injection technique is a medical technique to directly transmit medical drugs into a body of a patient by means of a catheter. Specifically, the intravenous injection technique includes a general intravenous injection technique and a central intravenous injection technique. As for the general intravenous injection technique, a needle of the catheter is penetrated into a vein vessel of an arm, a hand, a foot, an ankle or a head of the patient, an intravenous drip is performed by hanging an injection liquid to a higher position, and the injection liquid is directly transmitted into the blood vessels of the patient. As for the central intravenous injection technique, a needle of a central intravenous catheter is penetrated into a main line, for example, a jugular vein, a venae subclavia, or a femoral vein and the like, and a plurality of liquids are transmitted into the main line. Therefore, the central intravenous catheter technique also needs to be supplied with liquid frequently, and compared with the general intravenous injection technique, the transmission of the liquid takes a long time and the amount of the liquid is large.

During the operation of the two kinds of the intravenous injection techniques as described above, they all need to accurately penetrate the needle of the catheter into the vein, and after the penetration of the needle, the needles shall be kept within the vein always. However, during the entire process of intravenous infusion, it tends to take place the phenomenon of vein puncture of the needle or falling out of the vein for the needle, thereby resulting in leaking the drugs into body tissues surrounding the needle.

Currently, the leakage of the intravenous injection can only be inspected by a person, that is, after implementing a venepuncture for a period of time, once a skin of the patient at an acupuncture point presents bumps or water creeps, the leakage of the intravenous injection can only be noted. Due to different asymptomatic and presentations for different persons, with regards to some persons, the skin will present apparent bumps just after the leakage of the intravenous injection happens, so as to be observed easily. As for other persons, the skin will present bumps until the leakage of the intravenous injection has happened for a period of time, and at this time the leakage can be observed. Therefore, the detection by person's eyes to find out whether the leakage of the intravenous injection happens or not, may cause the problems that they cannot be discovered accurately and timely.

SUMMARY

An objective of the present application is to provide a detection system and a detection method for intravenous injection leakage, which is used to at least partially solve the problem that the intravenous injection leakage may not be detected accurately and timely.

In accordance with one aspect of the present application, it provides a detection system for intravenous injection leakage, comprising:

a detection module, configured to detect a status parameter of a skin at an acupuncture point; and an analysis module, configured to acquire the status parameter, and to determine whether the intravenous injection leakage happens or not, depending on the status parameter.

In accordance with another aspect of the present application, it provides a detection method for intravenous injection leakage, comprising the steps of:

detecting a status parameter of a skin at an acupuncture point;

determining whether the intravenous injection leakage happens or not, depending on the status parameter.

The detection system for intravenous injection leakage provided by the present application has the structure as described above. Because when the intravenous injection produces the leakage, the status parameter of the skin at the acupuncture point will change very rapidly. The present application determines whether the intravenous injection leakage happens or not, depending on the status parameter of the skin at the acupuncture point, and thus can timely find out the leakage of the intravenous injection, so that the leaked liquid would not be accumulated within the body tissue largely. Therefore, it can solve the problem that the liquid leakage of the intravenous injection cannot be accurately and timely in the prior art. The detection method for intravenous injection leakage will not be repeatedly discussed herein, due to having the same advantages as those of the detection system for intravenous injection leakage over the prior art.

BRIEF DESCRIPTION OF THE DRAWINGS

In order to better clearly explain the technical solutions of the embodiments of the present application, the drawings used for the embodiments are discussed briefly herein. Obviously, the following drawings are only directed to only one part of the embodiments, and the person skilled in the art can obtain other figures from the above drawings without any creative efforts.

EXPLANATION ABOUT REFERENCE SIGNS

Figure 1:
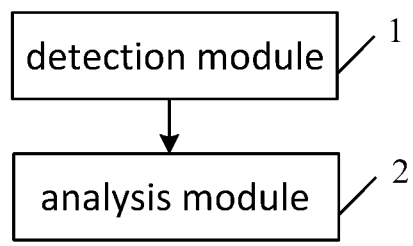
FIG. 1 is a schematic view of a detection system for intravenous injection leakage provided by a general concept of the present application.

1—detection module 11—temperature measuring module
111—visible light emitter

112—temperature measuring probe 12—electrical conductivity module
121—metal sensor pad 2—analysis module

DETAILED DESCRIPTION OF THE EMBODIMENTS

Technical solutions of the present application will be described more clearly and completely with reference to the drawings about embodiments of the present application. Obviously, the described embodiments are only a part of the embodiments of the present application, rather than all of the embodiments of the present application. Based on the embodiments of the present application, all of other embodiments which are derived by the person skilled in the art without any creative efforts, shall fall within the scope of the present application.

Prior to describing the embodiments, principles of the embodiments of the present application will be explained firstly, that is, a relationship between the intravenous injection leakage and a temperature or an electrical conductivity of the skin at an acupuncture point will be interpreted as follows:

I. Relationship of the Intravenous Injection Leakage and the Temperature of the Skin at the Acupuncture Point Normally, an interior tissue of a person's body has a temperature of a constant value, which is higher than a temperature of an ordinary liquid within an environment where the body is located. When a liquid for intravenous injection continuously enters into a vein, within the body tissue at the acupuncture point (a certain range within the needle as a center), a temperature of a linear body issue along a flowing direction of vein blood slowly changes gradually. When the liquid for intravenous injection is leaking out, since the leaked liquid accumulates within the body tissue near the needle, a temperature of blocky body tissue near the needle, within the body tissue at the acupuncture point will rapidly decrease. Because the skin is located close to the acupuncture point, when the intravenous injection leakage happens, illustratively, a temperature field parameter of the skin at the acupuncture point can be detected at once time, so as to determine temperature change of the temperatures of several points within the skin at the acupuncture point from the temperature at the needle. Illustratively, the temperature field parameter includes temperatures of several points within the skin at the acupuncture point, wherein said several points includes a point where the needle is located. Alternatively, the intravenous injection leakage can be determined based on whether the temperature changes of the skin along the flowing direction of the vein blood to be regular or not. Illustratively, the temperature field parameter includes temperatures of several points within the skin at the acupuncture point, wherein said several points do not include the point where the needle is located. In addition, the temperature filed parameter of the skin at the acupuncture point can be detected at multiple times, and the intravenous injection leakage is determined based on the changing ratio of the whole temperature field of the skin at the acupuncture point. As one example, the temperature field parameter can include a temperature of at least one point near the needle within the skin at the acupuncture point.

II. Relationship Between the Intravenous Injection Leakage and the Electrical Conductivity of the Skin at the Acupuncture Point In a normal condition, electrical conductivity of body's skin and muscle is within a certain range. When the liquid for the intravenous injection contains electrolyte for example normal saline, such liquid for intravenous injection will become a strong conductor for electricity and have a high electrical conductivity. Once the intravenous injection leakage happens, the leaked liquid will accumulate within the body tissue near the needle of the intravenous injection catheter, and result in an increase of the electrical conductivity at this position. When the liquid for intravenous injection contains pure water and non-electrolyte, for example, pure water and amylaceum, such liquid for intravenous injection is an insulator or a weak conductor for electricity and has a low conductivity. Once the intravenous injection leakage happens, the leaked liquid will accumulate within the body tissue near the needle of the intravenous injection catheter, and result in reduction of the electrical conductivity at this position. A distribution about the electrical conductivity field at the skin is directly subject to an influence of the electrical conductivity of the skin itself or the hypoderm tissue of the skin. Therefore, the intravenous injection leakage can be determined by detecting the change of the electrical conductivity field of the skin at the acupuncture point by the needle of the intravenous injection catheter. Illustratively, the electrical conductivity between any two adjacent points among several points of the skin at the acupuncture point is detected as the electrical conductivity field of the skin at the acupuncture point. Preferably, the above points are uniformly distributed within the skin at the acupuncture point. When the intravenous injection leakage happens, within the skin at the acupuncture point, the electrical conductivity between two points of the skin closest to the needle will change, and the electrical conductivity between any other two points of the skin will keep constant. Thus, it is possible to determine whether the intravenous injection to produce leakage or not, by detecting whether any electrical conductivity within the electrical conductivity field is changed or not. As another example, the electrical conductivity between any two points among points of the skin at the acupuncture point or the electrical conductivity between the two points of the skin at the acupuncture point is detected as the electrical conductivity field of the skin at the acupuncture point. When the intravenous injection leakage happens, it is feasible to determine whether the intravenous injection produces leakage or not, depending on the change of the entire electrical conductivity field.

An embodiment of the present application provides a detection system for intravenous injection leakage. As shown in FIG. 1, the detection system includes a detection module 1 and an analysis module 2. The detection module 1 is used to detect a status parameter of the skin at the acupuncture point; and the analysis module 2 is used to acquire the status parameter, and to determine the intravenous injection leakage happens or not, depending on the status parameter.

It should be noted that (1) the skin at the acupuncture point can be within a certain range with the acupuncture point as a center, and be meant to an epidermis, a derma or a subcutaneous tissue of the skin at the acupuncture point; (2) the communication between the detection module 1 and the analysis module 2 can be a wire communication or a wireless communication; and (3) the status parameter can include at least one of the temperature field parameter and the electrical conductivity field parameter.

An embodiment of the present application provides a detection system for intravenous injection leakage. The detection module 1 can in real time detect the status parameter of the skin at the acupuncture point, so that the analysis module 2 can in real time determine whether the intravenous injection leakage happens or not in accordance with the status parameter. Because the status parameter of the skin at the acupuncture point will change at the early stage of the injection liquid leakage, it may accurately and timely observe the intravenous injection liquid leakage, so that it can ensure the given dose of the injection liquid is achieved for the patient and the desired therapeutic effect is obtained.

In the above embodiment, the detection module 1 can have three kinds of structures, and in order to facilitate the skilled person to understand the present application, the three structures will be described in detail respectively.

Figure 2:
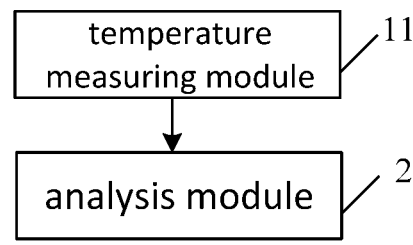
FIG. 2 is a schematic view of one specific example of the detection system for intravenous injection leakage as shown in FIG. 1.

Within the first kind of the structure, as shown in FIG. 2, the status parameter includes the temperature field parameter, and the detection module 1 includes a temperature measuring module 11, which is configured to detect the temperature field parameter of the skin at the acupuncture point. The analysis module 2 is specifically used to acquire the temperature field parameter and to determine whether the intravenous injection leakage happens or not, depending on the temperature field parameter. Illustratively, the temperature field parameter may include a temperature of at least one point adjacent to the needle within the skin at the acupuncture point, and then the temperature measuring module 11 detects the temperature of at least one point adjacent to the needle within the skin at the acupuncture point, thereby forming the temperature field parameter.

With the first kind of structure, the temperature measuring module 11 includes a contact type temperature measuring module or a non-contact type temperature measuring module. The contact type temperature measuring module makes a contact with the skin at the acupuncture point, whereas the non-contact type temperature measuring module does not contact the skin at the acupuncture point. Illustratively, the contact type temperature measuring module can be a pad-shaped thermometer covered onto the skin at the acupuncture point or a thermometer placed around the skin at the acupuncture point, as long as it can detect the temperature field of the skin at the acupuncture point.

Figure 3:
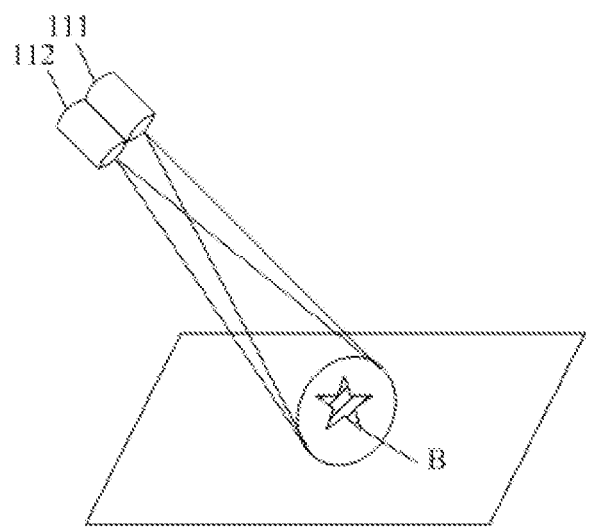
FIG. 3 is a schematic view of a temperature measuring module as shown in FIG. 2.

In the above embodiments, as shown in FIG. 3, the temperature measuring module 11 includes the non-contact type temperature measuring module, which includes a visible light emitter 111 and a temperature measuring probe 112. The visible light emitter 11 is used to illuminate the acupuncture point B, and to determine the position of the acupuncture point B. The temperature measuring probe 112 is used to detect the temperature field parameter of the skin at the acupuncture point B, depending on the position of the acupuncture point B. Specifically, the visible light emitter 111 can emit the light which can be identified by an eye of a person, so that a user (a nurse, a patient or a family member of the patient) can adjust an illuminating position and direction of the visible light emitter 111, as to enable the visible light emitter 11 to illuminate the acupuncture point B and to determine the position of the acupuncture point B. The temperature measuring probe 112 may be an infrared temperature measuring probe. In addition, the visible light emitter 111 and the temperature measuring module 112 can be two separate modules, or one module or assembly to be packaged together. This is not limited herein. The temperature measuring module 111 can be fixed around the patient by a bracket, or be held by a hand of the user. Preferably, the temperature measuring module 11 is fixedly set, which will not waste the labor. Because the temperature measuring module 11 is of contact type or non-contact type, this will detect the temperature of the skin at the acupuncture point without invading into the body tissue. This will not incur any harm to the patient, and is relatively simple.

In the above embodiment, the analysis module 2 is specified to acquire the temperature field parameter and to determine the intravenous injection to produce leakage or not by a classifier method depending on the temperature field parameter; or to acquire the temperature field parameter and to determine a probability that the intravenous injection leakage happens by a statistic regression method depending on the temperature field parameter, and when the probability is larger than a first threshold value, it is determined that the intravenous injection leakage happens.

It should be noted that firstly, the classifier is one kind of computing tool, which includes the specific classifiers such as a decision tree, a neural network, a linear classifier and a quadratic classifier or the like. It should be understood that the classifier includes many kinds of specific classifiers, and because it is known in the prior art, the present application does not make an exhaustive examples. Further, only several common specific classifiers are taken as the examples, but the present application does not make any limitation to this. It also should be noted that since the classifier is the existing common computing tool, only one kind of specific classifier is explained in detail illustratively in terms of working process. Other specific classifiers which are not shown exhaustively can be derived according to the prior art, and they are not repeatedly discussed herein.

In the above embodiment, illustratively, the step of determining whether the intravenous injection leakage happens or not by the classifier method depending on the temperature field parameter by means of the analysis module 2 includes the steps of: calculating the characteristics of the temperature field of the skin region at the acupuncture point by means of the analysis module 2 depending on the temperature field parameter measured at once time, so as to analyze the change of the temperature field, wherein when the change of the temperature field is abnormal, it is determined that the intravenous injection leakage happens; when the change of the temperature field is normal, it is determined that the intravenous injection leakage does not happen. Said temperature field parameter measured at once time can include temperatures of several points within the skin at the acupuncture point, and the several points include the point where the needle is located. Of course, the temperature field parameter measured at once time can also include the temperature parameter at other positions, as long as it can indicate the difference between the temperatures when the intravenous injection leakage happens and when the intravenous injection leakage does not happen. Illustratively, the temperature field parameter measured at once time includes temperatures of several points within the skin at the acupuncture point, wherein the several points do not include the point where the needle is located. Illustratively, the normal change of the temperature field and abnormal change of the temperature field can be as follows. When the temperature field parameter measured at once time includes the temperatures of points within the skin at the acupuncture point, the points include the point where the needle is located, and other points are located near the needle. The normal change of the temperature field means the significant decrease of the temperature along the flowing direction of the vein blood. This is because when the intravenous injection does not produce leakage, the temperature at the needle will decrease due to the lower temperature of the intravenous injection liquid, the points distributed along the flowing direction of the vein injection blood are influenced by the intravenous injection liquid to be small, so that they have higher temperatures, and thus the temperature changes very large along the flowing direction of the vein blood. The abnormal change of the temperature field can means not significant decrease along the flowing direction of the vein blood. This is because when the intravenous injection produces leakage, the leaked liquid covers the needle and the above several points, so that they have a little difference in terms of temperature, and thus the temperature change is relatively small along the flowing direction of the vein blood. In addition, as an example, the normal change of the temperature field and abnormal change of the temperature field can also be as follows. When the temperature field parameter measured at once time includes the temperatures of several points within the skin regions at the acupuncture point, the points do not include the point where the needle is located and are uniformly distributed within the skin at the acupuncture point, the normal change of the temperature field is the small change of the temperature along the flowing direction of the non-vein blood. This is because when the intravenous injection does not produce leakage, the temperatures of the skin at the acupuncture point are substantively identical. The abnormal change of the temperature field can be relatively large change along the flowing direction of the non-vein blood. This is because the points which are covered by the intravenous injection liquid have lower temperatures, and points which are not covered by the intravenous injection liquid have higher temperatures, thereby the temperature change along the flowing direction of the non-vein blood is relatively large. It can be seen from the above that when the temperature parameter measured by once time is different, the change of the temperature field presented by the intravenous injection leakage is also different. Although the present application is not explained exhaustively on this point, it is obvious that various conditions of the changes of the temperature field presented by the intravenous injection leakage can be derived by the disclosed as described above.

Because in the case that the temperature field parameter measured at once time includes different parameters, the methods for determining whether the intravenous injection leakage happens or not are substantially identical to each other; the classifier method is explained taking the classifier is specified as the linear classifier, the temperature field parameter measured at once time includes temperatures of several points within the skin region at the acupuncture point, and the several points include the point where the acupuncture point is located as one example. It should be noted that before inputting the temperature field parameter into the classifier, parameters w, b of the linear classifier should be obtained by stimulation experiments, that is, the parameters of the liner classifier are obtained by taking comprehensive consideration about various temperature distributions when the intravenous injection produces leakage and does not produce leakage. In one example, w represents a vector of a projection direction, and b represents a scalar of an offset. Then, based on the obtained temperature field parameter, a gradient of the temperature field (a change of the temperature within a unit distance along a certain direction) and temperature difference between the temperature of each point within the skin at the acupuncture point and the temperature of the point where the needle is located, are obtained. $t(x, p)$ can be used to represent the temperature difference between the temperature of each point within the skin at the acupuncture point and the temperature of the point where the needle is located, wherein X represents a temperature of one point within the skin region at the acupuncture point, p represents a temperature of the point where the needle is located. After that, the obtained gradient of the temperature field and the temperature difference from the each point to the needle are cascaded as one vector v, and an output $f=w'\cdot v+b$ is calculated, wherein ' is a transpose symbol. When the change of the temperature field is abnormal, $f>0$, the output of the linear classifier is larger than 0, thereby determining the intravenous injection leakage happens; and when the change of the temperature field is normal, $f\leq 0$, the output of the linear classifier is less than or equal to 0, thereby determining the intravenous injection leakage does not happen.

Secondly, the statistic regression method is one method which includes a linear regression, a logic regression and a decision tree based regression method, and the like. The statistic regression method is adapted to the case that the temperature field parameter includes a temperature of at least one point within the skin at the acupuncture point adjacent to the needle. Illustratively, determining whether the intravenous injection leakage happens or not by means of the analysis module 2 depending on the temperature field parameter with the statistic regression method is: the analysis module 2 analyzes the whole change ratio of the temperature field parameter depending on the temperature field parameter measured multiple times, and calculates the probability that the intravenous injection leakage happens. When the probability is larger than a first threshold, the intravenous injection leakage is determined to do happen. Illustratively, the temperature field parameter on the whole changes more rapidly, the probability that the intravenous injection leakage happens is higher.

Thirdly, the first threshold can be determined according to actual needs. Illustratively, if the leakage of the intravenous injection liquid is harmful to the body, then the first threshold is set to be small. Illustratively, the first threshold is set to be 0.2. When the probability that the intravenous injection liquid is leaked is larger than 0.2, the intravenous injection liquid is determined to be leaked. If the procedure of penetrating the needle of the intravenous injection catheter into the vein of the patient is complicated, and the leakage of the intravenous injection liquid is not harmful to the body, then the first threshold is set to be relatively large. Illustratively, the first threshold is set to be 0.5. Since the value of the probability is in a range of 0-1, the value of the first threshold is also in a range of 0-1. In addition, the above classifier method and the statistic regression method can be used separately, or can be used in conjunction with each other.

The principle that the analysis module 2 achieves the judgment about the intravenous injection leakage in the above embodiments is: to utilize the change of the temperature field of the skin along the flowing direction of the vein blood within the skin at the acupuncture point to be abnormal or not in the case that the intravenous injection leakage happens, or to utilize the change ratio of the temperature field of the skin at the acupuncture point in the case that the intravenous injection leakage happens, so as to achieve the judgment about the intravenous injection leakage.

Figure 4:
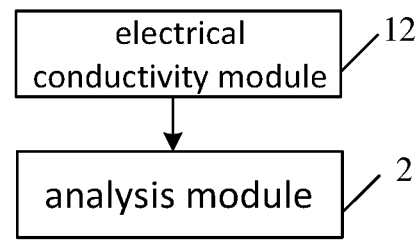
FIG. 4 is a schematic view of another specific example of the detection system for intravenous injection leakage as shown in FIG. 1.

In the second structure, as shown in FIG. 4, the status parameter includes an electrical conductivity field parameter. The detection module 1 includes an electrical conductivity module 12, used to detect the electrical conductivity field parameter of the skin at the acupuncture point. The analysis module 2 is specified to acquire the electrical conductivity field parameter and to determine whether the intravenous injection leakage happens or not depending on the electrical conductivity field parameter. The electrical conductivity field parameter is an assemblage of the electrical conductivity fields between any two adjacent points among several points of the skin at the acupuncture point.

Preferably, the several points are uniformly distributed within the skin at the acupuncture point. In addition, the electrical conductivity filed parameter can also be the electrical conductivity between the two points. It should be noted that when the electrical conductivity field parameter is the electrical field between two points, the two points are adjacent to the needle.

Figure 5:
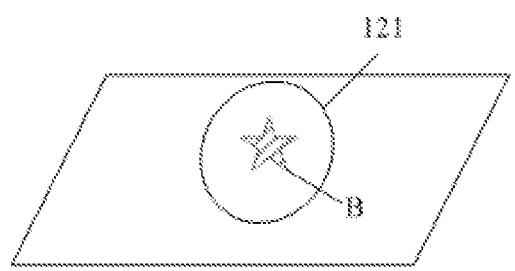
FIG. 5 is a schematic view of an electrical conductivity module as shown in FIG. 4.

The electrical conductivity module 12 is a contact type electrical conductivity module, which makes a contact with the skin at the acupuncture point. Illustratively, as shown in FIG. 5, the electrical conductivity module includes a metal sensor pad 121, which covers the skin at the acupuncture point B, and detects the electrical conductivity field of the subcutaneous tissue at the acupuncture point B. The metal sensor pad 121 can detect the electrical conductivity between two points of the subcutaneous tissue at the acupuncture point B, by positioning the two points onto the skin at the acupuncture point B, thereby obtaining the electrical conductivity field parameter of the skin at the acupuncture point B. Alternatively, the metal sensor pad 121 can detect the electrical conductivity between any two adjacent points of the subcutaneous tissue at the acupuncture point B, by positioning a plurality of the two adjacent points among the several points onto the skin at the acupuncture point B, thereby obtaining the electrical conductivity field parameter of the skin at the acupuncture point B.

In the above embodiments, the analysis module 2 is specified to acquire the electrical conductivity field parameter, and to determine whether the intravenous injection leakage happens or not by the classifier method depending on the electrical conductivity field parameter; or to acquire the electrical conductivity field parameter, and to calculate the probability that the intravenous injection leakage happens by the statistic regression method depending on the electrical conductivity field parameter, wherein when the probability is larger than the second threshold, the intravenous injection leakage is determined to do happen.

It should be noted that firstly, the classifier method is applied to the case that the electrical conductivity field parameter is an assemblage of the electrical conductivities between any two adjacent points among several points of the skin at the acupuncture point. Illustratively, the step of determining whether the intravenous injection leakage happens or not by means of the analysis module 2 depending on the electrical conductivity field parameter with the classifier method may be: depending on the electrical conductivity field parameter measured at once time, to analyze the gradient change of the electrical conductivity field parameter by the analysis module 2, wherein when the gradient change of the electrical conductivity field parameter is abnormal, the intravenous injection leakage is determined to do happen and at this time the output of the classifier is 1. Illustratively, the abnormal gradient change of the electrical conductivity field parameter is meant to the electrical conductivity between any two points within the electrical conductivity field parameter different from the electrical conductivity between other two points. When the gradient change of the electrical conductivity field parameter is normal, the intravenous injection leakage is determined to do not happen, and at this time, the output of the classifier is 0. Illustratively, the normal gradient change of the electrical conductivity field parameter is meant to the electrical conductivities of all of the two points within the electrical conductivity field parameter to be identical.

Secondly, the statistic regression method is applicable to the condition that the electrical conductivity parameter is the assemblage of the electrical conductivity fields between any two adjacent points among the several points of the skin at the acupuncture point or is the electrical conductivity between two points. Illustratively, the step of determining whether the intravenous injection leakage happens or not by means of the analysis module 2 depending on the electrical conductivity field parameter with the statistic regression method is: depending on the electrical conductivity field parameters measured by multiple times, to analyze the change of the whole of the electrical conductivity fields, and thus to calculate the probability that the intravenous injection leakage happens, wherein when the probability is larger than the second threshold, the intravenous injection leakage is determined to do happen. Illustratively, as the speed of the whole change of the electrical conductivity field parameters increased, the probability that the intravenous injection leakage happens is enhanced. Alternatively, if the conditions that the electrical conductivities between two points among the several points change are increased, the probability that the intravenous injection leakage happens will become enhanced. The setting method of the second threshold can be made reference to that of the first threshold, and they are not discussed again. In addition, the classifier method and the statistic regression method can be used separately or in conjunction with each other.

The principle that the analysis module 2 achieves the judgment about the intravenous injection leakage in the above embodiments is: to utilize whether the electrical conductivity fields between any two points within the skin at the acupuncture point to be abnormal or not in the case that the intravenous injection leakage happens; or to utilize whether the whole of the electrical conductivity fields of the skin at the acupuncture point to change abnormally or not in the case that the intravenous injection leakage happens, so as to achieve the judgment about the intravenous injection leakage.

Figure 6:
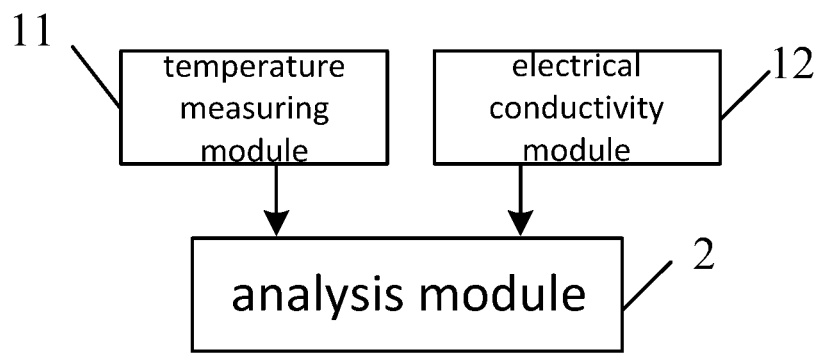
FIG. 6 is a schematic view of a further specific example of the detection system for intravenous injection leakage as shown in FIG. 1.

In the third structure, as shown in FIG. 6, the status parameter includes a temperature field parameter and an electrical conductivity field parameter. The detection module 1 includes a temperature measuring module 11 and an electrical conductivity module 12. The temperature measuring module 11 is used to detect the temperature field parameter of the skin at the acupuncture point; and the electrical conductivity module 12 is used to detect the electrical conductivity field parameter of the skin at the acupuncture point. The analysis module 2 is specified to acquire the temperature field parameter and the electrical conductivity field parameter, and to determine whether the intravenous injection leakage happens or not depending on the temperature field parameter and the electrical conductivity field parameter.

It should be noted that since the temperature measuring module 11 or the electrical conductivity module 12 might not detect the parameter, the analysis module 2 can determine whether the intravenous injection leakage happens or not depending on one of the temperature field parameter and the electrical conductivity field parameter, or both of them.

In the third structure, the arrangement and function of the temperature measuring module 11 can be found from those of the temperature measuring module 11 in the first structure; and the arrangement and function of the electrical conductivity module 12 can be found from those of the electrical conductivity module 12 in the second structure. Therefore, they are not discussed herein again.

In the third structure, the analysis module 2 is specified to acquire the temperature field parameter and the electrical conductivity field parameter, and to determine whether the intravenous injection leakage happens or not depending on the temperature field parameter and the electrical conductivity field parameter with the classifier method; or to acquire the temperature field parameter and the electrical conductivity field parameter, and to calculate the probability that the intravenous injection leakage happens depending on the temperature field parameter and the electrical conductivity field parameter with the statistic regression method, and when the probability is larger than the third threshold, the intravenous injection leakage is determined to do happen.

It should be noted that firstly, the classifier method is applicable to the case that the temperature field parameter measured at once time and the electrical conductivity field parameter measured at once time are both included within the parameter assemblage. Illustratively, the temperature field parameter includes the temperatures of several points within the skin at the acupuncture point, and the electrical conductivity field parameter is the assemblage of the electrical conductivities between any two adjacent points among the several points. Preferably, in order to ensure the judgment result to be true, within the parameter assemblage, the temperature field parameter measured at once time and the electrical conductivity field parameter measured at once time are measured at the same time. Illustratively, the step of determining whether the intravenous injection leakage happens or not by means of the analysis module 2 depending on the temperature field parameter and the electrical conductivity field parameter with the classifier method may be: depending on the parameter assemblage measured at once time, to analyze an integrated gradient change of both the temperature field parameter and the electrical conductivity field parameter by the analysis module 2. When the integrated gradient change is abnormal, the intravenous injection leakage is determined to do happen, and at this time the output of the classifier is larger than 0. Illustratively, the abnormal change of the integrated gradient is meant to no significant decrease of the temperatures within the temperature field parameter along the flowing direction of the vein blood, and the electrical conductivity between any two points within the electrical conductivity field parameter is different from that between other two points, that is, the abnormal change of the integrated gradient is meant to both the abnormal gradient change of the temperature field parameter and the abnormal gradient change of the electrical conductivity field parameter. When the change of the integrated gradient is normal, the intravenous injection leakage is determined to do happen, and at this time, the output of the classifier is smaller than or equal to 0.

Secondly, the statistic regression method is applicable to the case that the temperature field parameter measured at once time and the electrical conductivity field parameter measured at once time are included within the parameter assemblage. The temperature field parameter includes the temperature of at least one point within the skin at the acupuncture point adjacent to the needle, and the electrical conductivity field parameter is the assemblage of the electrical conductivities between any two adjacent points among the several points, and the electrical conductivity between two points. Preferably, in order to ensure the judgment result to be true, within the parameter assemblage, the temperature field parameter measured at once time and the electrical conductivity field parameter measured at once time are measured at the same time. Illustratively, the step of determining whether the intravenous injection leakage happens or not by means of the analysis module 2 depending on the temperature field parameter and the electrical conductivity field parameter with the statistic regression method may be: depending on the parameter assemblage measured by multiple times, to analyze an integrated change of both the temperature field parameter and the electrical conductivity field parameter by the analysis module 2, and thus to calculate the probability that the intravenous injection leakage happens, wherein the probability is larger than the third threshold, the intravenous injection leakage is determined to produce leakage. Illustratively, as the speed of the whole change of the temperature field parameter increases and/or the speed of the whole change of the electrical conductivity field parameter increases, the probability that the intravenous injection leakage happens is enhanced. The setting method about the third threshold can be made reference to that of the first threshold, and they are not discussed herein again. In addition, the classifier method and the statistic regression method can be used separately or in conjunction with each other.

Compared with the first and second structures in which a single parameter is used to determine whether the intravenous injection leakage happens or not, the third structure employs the temperature field parameter and the electrical conductivity field parameter together to determine whether the intravenous injection leakage happens or not, and thus it can more accurately determine whether the intravenous injection leakage happens or not. Therefore, it is preferable to use the detection system having the third structure provided by the present embodiment of the present application.

Within the three structures, the detection system may further include an alarm module connected with the analysis module 2. When the analysis module 2 determines the intravenous injection to produce leakage, it will send an alarm signal to the alarm module, so that the alarm module can make an alarm. The alarm module and the analysis module 2 can be communicated by means of a wire or wireless manner. The alarm module can be provided within a ward of the patient, so as to enable the patient or the family members of the patient to pull out the catheter from the skin of the patient. Alternatively, the alarm module can also be provided within a nurse station, so as to inform a nurse to treat it.

In the above embodiment, the detection system further includes an online module connected with the detection module 1 and the analysis module 2 respectively, and used to acquire the status parameter detected by the detection module 1, and the judgment result of the analysis module 2, and to send the status parameter and the judgment result to a server accordingly. It should be noted that firstly, the online module can be communicated by a wire or wireless manner to the detection module 1 or the analysis module 2; secondly, the online module can be placed within the ward of the patient, so as to receive the relevant parameter and send it to the server within the nurse station, so as to facilitate the nurse's monitoring; and thirdly, the online module can also be placed within the server within the nurse station, so as to receive the relevant parameters, and to display it by a display module of the server, thereby facilitating the nurse's monitoring.

Figure 7:
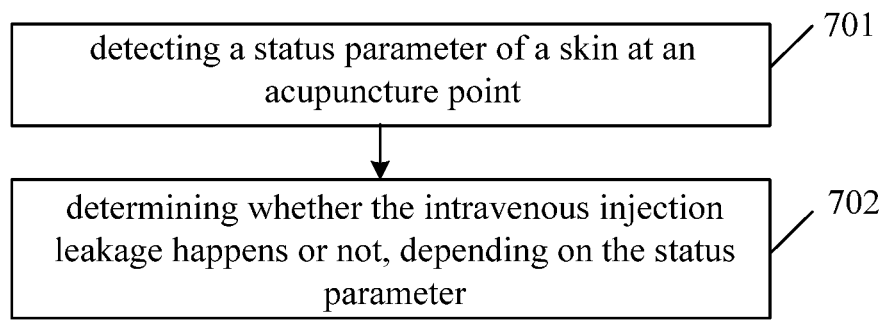
FIG. 7 is a flowchart of a detection method for intravenous injection leakage provided by an embodiment of the present application.

Another embodiment of the present application is to provide a detection method for the intravenous injection leakage, as shown in FIG. 7, including:

Step 701, detecting the status parameter of the skin at the acupuncture point. Illustratively, in conjunction with the explanation about FIG. 1, the status parameter of the skin at the acupuncture point is detected by the detection module 1.

Step 702, determining whether the intravenous injection leakage happens or not, depending on the status parameter. Illustratively, in conjunction with the explanation about FIG.

1, the analysis module 2 is used to determine whether the intravenous injection leakage happens or not, depending on the status parameter.

An embodiment of the present application provides a detection method for intravenous injection leakage, which can in real time detect the status parameter of the skin at the acupuncture point, and determine whether the intravenous injection leakage happens or not depending on the status parameter. Because the change of the status parameter can be found out in the case that the intravenous injection liquid is not accumulated too much, it can timely find out the intravenous injection leakage, and it can ensure the patient to obtain the given dose of the injection liquid, thereby achieving the therapeutic effect.

Illustratively, the status parameter includes a temperature field parameter, and the step 701 specifically includes detecting the temperature field parameter of the skin at the acupuncture point. Illustratively, in conjunction with the explanation about FIG. 2, the temperature measuring module 11 detects the temperature field parameter of the skin at the acupuncture point. The step 702 specifically includes determining whether the intravenous injection leakage happens or not depending on the temperature field parameter.

In the above embodiment, the step of detecting the temperature field parameter of the skin at the acupuncture point specifically includes: illuminating the acupuncture point with the visible light; determining the position of the acupuncture point; detecting the temperature field parameter at the acupuncture point. Illustratively, in conjunction with the explanation about FIG. 3, the visible light emitter 111 is used to illuminate the acupuncture point with the visible light; and to determine the position of the acupuncture point. The temperature measuring module 112 is used to detect the temperature field parameter at the acupuncture point depending on the position of the acupuncture point.

Illustratively, the status parameter includes an electrical conductivity field parameter, and the step 701 specifically includes detecting the electrical conductivity field parameter of the skin at the acupuncture point. Illustratively, in conjunction with the explanation about FIG. 4, the electrical conductivity module 12 detects the electrical conductivity field parameter of the skin at the acupuncture point. The step 702 specifically includes determining whether the intravenous injection leakage happens or not depending on the electrical conductivity field parameter.

Illustratively, the status parameter includes a temperature field parameter and an electrical conductivity field parameter, and the step 701 specifically includes detecting the temperature field parameter and the electrical conductivity field parameter of the skin at the acupuncture point. Illustratively, in conjunction with the explanation about FIG. 6, the temperature measuring module 11 detects the temperature field parameter of the skin at the acupuncture point, and the electrical conductivity module 12 detects the electrical conductivity field parameter of the skin at the acupuncture point. The step 702 specifically includes determining whether the intravenous injection leakage happens or not depending on the temperature field parameter and the electrical conductivity field parameter.

In the above embodiment, after the step 701, the method further includes sending the status parameter to the sever. After the step 702 of determining whether the intravenous injection leakage happens or not, the method further includes sending the judgment result to the sever. In addition, after determining the leakage of the intravenous injection, it can further include sending out the alarm signal.

Various embodiments of the present application are described in a way of progressive mode, the same or similar parts between respective embodiments can be referred to each other, and the part of each embodiment to be emphasized is the difference of it from other embodiments. Especially, as for the embodiment of the method, it is described very simple due to substantively similar to the embodiment of the product. The relevant parts of the method can be found from the corresponding part of the embodiment of the product.

It should be noted that the embodiments of the system as described above are only illustrative, in which the units to be interpreted as the separate parts can be or be not separated physically. The parts shown as the units can be or can be not the physical units, that is, being located at one place, or distributed onto a plurality of units. Objectives of the technical solutions of the present embodiment can be achieved by selecting a part or all of the modules according to actual needs. The person skilled in the art can understand and implement it without any creative work.

The above embodiments are the preferred embodiments of the present application, and are not used to limit the present application. It should be noted that various modifications and changes may be made to the present disclosure by those skilled in the art without departing from the principles and spirit of the present application. As such, these modifications and changes to the present application are also intended to be included within the present application if they fall within the scopes of the present application defined by claims and equivalents thereof.

What is claimed is:

1. A detection method for intravenous injection leakage during an intravenous injection, comprising steps of:
   detecting a status parameter of a skin at an acupuncture point,
      wherein the status parameter comprises a temperature field parameter and an electrical conductivity field parameter,
      wherein the temperature field parameter is a parameter of a temperature field and comprises temperatures of a first plurality of points within the skin at the acupuncture point that are uniformly distributed within the skin at the acupuncture point, and
      wherein the electrical conductivity field parameter is a parameter of an electrical conductivity field and comprises electrical conductivity between each two adjacent points among a second plurality of points within the skin at the acupuncture point making up the electrical conductivity field;
   determining a change of the temperature field based on a gradient of the temperature field along a flowing direction of vein blood and a temperature difference between the temperature of each of the first plurality of points within the skin and the temperature of the point where the needle is located;
   determining a gradient change of the electrical conductivity field based on a gradient of the electrical conductivity field parameter;
   identifying the intravenous injection leakage when (1) the change of the temperature field is above a predetermined threshold and (2) a presence of the gradient change of the electrical conductivity field;
   monitoring the intravenous injection and outputting an alarm for a user to treat the identified intravenous injection leakage.

2. The detection method as claimed in claim 1, wherein the step of detecting the temperature field parameter of the skin at the acupuncture point comprises:
   illuminating the acupuncture point with a visible light, and determining a position where the acupuncture point is located; and
   detecting the temperature field parameter at the acupuncture point depending on the position where the acupuncture point is located.

3. The detection method as claimed in claim 1, wherein after detecting the status parameter of the skin at the acupuncture point, the method further comprises sending the status parameter to a server.

4. The detection method as claimed in claim 3, wherein after determining that the intravenous injection leakage happens, the method further comprises sending a judgment result to the server.

\* \* \* \* \*